United States Patent [19]

Laby

[11] Patent Number: 4,671,789
[45] Date of Patent: Jun. 9, 1987

[54] CONTROLLED RELEASE COMPOSITIONS FOR ADMINISTRATION OF THERAPEUTIC AGENTS TO RUMINANTS

[75] Inventor: Ralph H. Laby, Canterbury, Australia

[73] Assignee: Commonwealth Scientific and Industrial Research Organization, Australia

[21] Appl. No.: 764,133

[22] Filed: Aug. 9, 1985

Related U.S. Application Data

[63] Continuation-in-part of Ser. No. 627,460, Jul. 3, 1984, abandoned, which is a continuation of Ser. No. 355,740, Jul. 2, 1981, abandoned.

[30] Foreign Application Priority Data

Jul. 2, 1980 [AU] Australia .................. PE4333

[51] Int. Cl.$^4$ .............................. A61K 47/00
[52] U.S. Cl. ...................... 604/59; 604/93; 604/891; 604/890; 604/135
[58] Field of Search ................. 424/19–22, 424/359; 604/890–892, 135, 134, 57, 59, 93

[56] References Cited

U.S. PATENT DOCUMENTS

| | | |
|---|---|---|
| 3,330,729 | 7/1967 | Johnson, Jr. |
| 3,656,483 | 4/1972 | Rudel . |
| 4,044,119 | 8/1977 | Carlson, Jr. et al. |
| 4,226,849 | 10/1980 | Schor . |

FOREIGN PATENT DOCUMENTS

| | | |
|---|---|---|
| 42008/58 | 4/1959 | Australia . |
| 4681/61 | 5/1961 | Australia . |
| 64414/60 | 9/1962 | Australia . |
| 23857/62 | 5/1964 | Australia . |
| 46076/64 | 12/1965 | Australia . |
| 16648/70 | 4/1971 | Australia . |
| 35908/78 | 11/1979 | Australia . |
| 1073358 | 3/1980 | Canada . |
| 0016652 | 10/1980 | European Pat. Off. . |
| 2443244 | 7/1980 | France . |
| 1504553 | 3/1978 | United Kingdom . |

OTHER PUBLICATIONS

DK ester literature submitted in Ser. No. 355,740.

Primary Examiner—C. Fred Rosenbaum
Assistant Examiner—Sherri Vinyard
Attorney, Agent, or Firm—Bacon & Thomas

[57] ABSTRACT

A controlled release composition for administering a therapeutic agent to a ruminant, using an intraruminal device, consists of a compressed tablet or bolus which comprises the therapeutic and a carrier material is formed from a non-tacky free flowing powder in which 90% of the particles are less than 100 $\mu$m (200 mesh sieve) and which can be mixed with the therapeutic agent to give a uniform, intimate and reproducible mixture such that when the tablet or bolus contacts an aqueous medium a fluid from the aqueous medium is absorbed at the tablet/aqueous medium interface into the body of the tablet to a predetermined depth of penetration so as to produce a gelled volume contiguous with the interface corresponding to the depth of penetration of the fluid, said gel hindering further penetration of the fluid into the tablet beyond the prearranged depth in order to maintain the rate of fluid penetration constant and the integrity of the tablet beyond the prearranged depth of penetration of the fluid to prevent release of therapeutic agent therefrom and said gel having a yield stress which is substantially less than the yield stress of the corresponding volume of the tablet before gelling and which sharply declines with increasing water content up to a preselected critical water content thereby permitting controlled release of therapeutic agent from the gel in use.

22 Claims, 5 Drawing Figures

CONTROLLED RELEASE COMPOSITIONS FOR ADMINISTRATION OF THERAPEUTIC AGENTS TO RUMINANTS

This application is a continuation-in-part of application Ser. No. 627,460 filed 3rd July, 1984 which is a continuation of application Ser. No. 355,740 filed 2nd July, 1981 now abandoned.

This invention relates to improvements in controlled-release compositions for administration of therapeutic agents to ruminants, and in particular the carrier materials used in such compositions. In accordance with the present invention it is now possible to regulate the rate of which a therapeutic material is administered by the selection of a suitable carrier material which both allows administration at a preselected controlled rate by dissolving on the one hand and preventing administration by not dissolving on the other hand. The controlled rate of dissolution is achieved by carefully controlling the gelling rate of the therapeutic composition.

The applicant's Australian Pat. No. 520409 describes a intraruminal device (IRD) intended for use in the controlled release administration of a wide range of biologically active, powdered, therapeutic agents. In that device (which is described in more detail hereinafter), a therapeutic agent of choice is suspended in a cylindrical matrix of surface active agents which is solid at the rumen temperature (39° C.). The cylindrical matrix is placed in the cylindrical barrel of an IRD with one end face held against an orifice at one end of the IRD. A pair of plastic arms extend from one end of the IRD at 90° C. to the axis of the IRD for the purpose of retaining the device in the reticulorumen. For oral administration, these arms are held against the barrel of the IRD by the action of water dispersible or disruptable tape.

As described in Australian Pat. No. 520409, the matrix is prepared by melting the surface active agents, incorporating the therapeutic agent in the molten material and casting the matrix core either directly in the barrel of the IRD or in a cylindrical mould for transfer to the IRD after solidification.

The selection of suitable surfactants and mixtures for use in the applicant's earlier invention is dependent upon (i) the melting range and (ii) properties IRD. In most instances, this form of matrix production has proved satisfactory, but, since 1978 an important series of failures of this technique has stimulated further development leading to this present application.

The therapeutic agent "Elfazepam" (Smith Kline Animal Health Products) dissolved in most matrix surfactants above 60° C. particularly the preferred surfactant at that time, Teric 18M2 (ICI Australia Ltd.) and recrystallized on cooling giving massive crystals. The resultant dissolution rates were very variable and quite unsatisfactory. The flukicide "Diamphenethide" (Wellcome Ltd.) also recrystallized from Teric 18M2 to give a mat of long, fine crystals which caused the dissolution of matrix to cease shortly after insertion when the crystals formed a fleted mass at the dissolution orifice. A developmental therapeutic agent reacted chemically with Teric 18M2 at 60° C. and the resultant product remained liquid on cooling to room temperature. These problems limit the potentially wide-ranging applicability of our earlier invention and requires alternative means of matrix production.

It has now been found that very satisfactory matrix cores can be made, even with the troublesome therapeutic agents mentioned above, by mixing the selected therapeutic agent with a powdered support or carrier material and forming the mixture into a tablet or bolus such as by pressing the powder mixture in a cylindrical die to form the tablet or bolus.

A number of powdered materials have been tested and found to be useful as the carrier material. While it is not possible to specify the suitable materials generically in orthodox physical or chemical terms, the following limitations provide a guide to the selection of suitable carrier materials.

(i) It must have a softening point in excess of 39° C.
(ii) It must be, or be capable of being milled to, a non-tacky free flowing powder in which 90% of the particles are less than 100 (200 mesh sieve), and which can be freely mixed with a therapeutic agent to give uniform, intimate and reproducible mixtures, which together with such bonding and slip agents as are necessary, are capable of forming a coherent tablet or bolus in a die under pressure.
(iii) It should preferably be a surface active material or emulsifying agent, or a material which behaves as such.
(iv) It must be generally regarded as safe by the appropriate regulatory authorities; preferably with clearance as a food grade material.
(v) The resultant core must show the required controlled release characteristics in the IRD of reproducibility of output, linearity of output, and required lifetime or release rate.

It is to be noted that the above are preferred characteristics of the carrier material and other carrier materials not possessing all of the above properties fall within the scope of the present invention.

Property (v) above is probably the more important requirement to be possessed by the carrier and is met by selecting a carrier material which when tableted and contacted with an aqueous medium absorbs a fluid such as water at the tablet/water interface, to produce swelling of the material and a resulting water gel. This behaviour is accompanied by marked changes in rheological properties, particularly yield stress and visco-elastic properties of the material. There is rapid reduction in viscosity and critical yield stress due to water absorption up to a particular water content at which the gel forms, after which further water absorption results in only a gradual reduction of viscosity and the gelled area acts as a barrier against further water absorption.

There is thus a sharp discontinuity in rheological properties at the critical water content and provided this discontinuity occurs at a pressure within the pressure range exerted by the drive spring of the IRD and at a water content which can be achieved in a portion of the core material which is in close proximity to the release orifice of the IRD, this phenomenon allows the soft water gel structures to be extruded from the capsule orifice by the action of the spring.

Additionally, water gels reduce the rate of water penetration into the matrix and thus an equilibrium is reached between the formation of the low viscosity gel and the driving spring force. The overall result of this combination parameters is a high precision of release, and extrusion of the matrix under the influence of the drive spring is sharply limited by the abrupt rheological discontinuity.

Therefore it is an object of the present invention to provide a therapeutic agent in admixture with a suitable carrier with gelling properties which permit controlled release of the therapeutic agent from the gel but prevent the formation of too much gel. Accordingly, the present invention provides a controlled release composition for administering a therapeutic agent to a ruminant comprising the therapeutic agent and a carrier material in the form of a coherent tablet or bolos in solid form, wherein said carrier material is formed from a non-stocky free flowing powder in which 90% of the particles are less than 100 m (200 mesh sieve) and which can be mixed with the therapeutic agent to give a uniform, intimate and reproducible mixture such that unless the tablet or bolus contacts an aqueous medium a fluid from the aqueous medium is absorbed at the tablet/aqueous medium interface into the body of the tablet to a predetermined depth of penetration so as to produce a gelled area contiginous the interface corresponding to the depths of penetration of the fluid, said gelled area preventing or hindering further penetration of the fluid into the tablet beyond the prearranged depth in order to maintain the integrity of the tablet beyond the prearranged depth of penetration of the fluid so as to prevent release of therapeutic agent therefrom and said gelled area having a critical yield stress which is substantially less than the critical yield stress of the corresponding area of the tablet before gelling and which sharply declines with increasing water content up to a preselected critical water content thereby permitting controlled release of therapeutic agent from the gelled area.

In accordance with another aspect of the present invention there is provided an intraruminal device for administering a therapeutic agent to a ruminate comprising a hollow body having an opening located at one end, a solid tablet or bolus comprising the therapeutic agent and a carrier material contained within the body, a driving means for urging the tablet or bolus towards the opening, restricting means adjacent the opening for preventing expulsion of ungelled tablet or bolus from the device by said driving means, and retaining means connected to the body for retaining the device in the rumen of the ruminant after location therein said carrier material is formed from a non-stocky free flowing powder in which 90% of the particles are less than 100 (200 mesh sieve) and which can be mixed with the therapeutic agent to give a uniform, intimate and reproducible mixture such that when the table or bolus contacts an aqueous medium a fluid from the aqueous medium is absorbed at the tablet/aqueous medium interface into the body of the tablet to a predetermined depth of penetration so as to produce a gelled are contiguous the interface corresponding to the depth of penetration of the fluid, said gelled area preventing or hindering further penetration of the fluid into the tablet beyond the prearranged depth of penetration of the fluid so as to prevent release of the therapeutic agent therefrom and said gelled are having a critical yield stress which is substantially less than the critical yield stress of the corresponding area of the tablet before gelling and which sharply declines with increasing water content up to a preselected critical water content thereby permitting controlled release of the therapeutic agent from the gelled area.

Selection of surfactant materials having the above properties can be easily made on the basis of simple experiments, details of which are given hereinafter.

As an example of one particularly satisfactory matrix material, we have found that the sucrose esters described in Dai-Ichi Kogyo Seitka Co. Ltd., Tokyo, Japan and prepared by the Nebraska-Snell process (U.S. Pat. No. 3,480,616), particularly "DK-Ester-F160", (containing 70% monostearate ester) made excellent matric cores, by the materials described in the previous paragraph and all other therapeutic agents used in our research.

DK-Ester is the tradename for purified grade sucrose fatty acid esters. Thus, for example the monostearate ester "DK-Ester-F160" is a compound of the formula:

This development can be contrasted with the process described in Australian Pat. No. 520409 because (i) the surfactants described in this patent are not powders but are waxy materials unsuitable for compressed table formation (ii) the sucrose esters used in the present invention melt with decomposition and are unsuitable for cast core formation, and (iii) DK-ester-F160 has an HLB of 15, well above the limit of 8.5 given in our earlier patent. This last point is the first of a series of unexpected discoveries arising from our investigations of the use of sucrose esters. Surface active agents of the type discussed in Pat. No. 520409, (i.e. nonionic ethylene oxide adducts of fatty acids and fatty amines) but with an HLB near 15 would dissolve under the conditions of the rumens of sheep and cattle so rapidly that an IRD based on them could not be expected to last for more than a few hours, whereas IRD's based on DK-ester-F160 can last for considerably more than 100 days, as shown in following examples. At this time we do not have an explanation for this extraordinary difference. Apart from DK-ester-F160, we have also found that other sucrose esters produced by the Dai-Ichi Company, which range in HLB frcm 1 to 15, can be used alone or in combination to produce compressed powder cores, in accordance with this invention, for use in IRD's.

Investigations have also shown that other classes of materials are suitable for use in the invention. For example, we have found that milk powder is a suitable support agent for very satisfactory cores of 6–10 day lifetime, at the present stage of development.

Another class of material which has given satisfactory results in the polyglycerol stearates, specifically the food-grade product CRESTER KZ (Croda).

The invention is further described and elucidated by reference to the accompanying drawings in which.

Figure 2A:
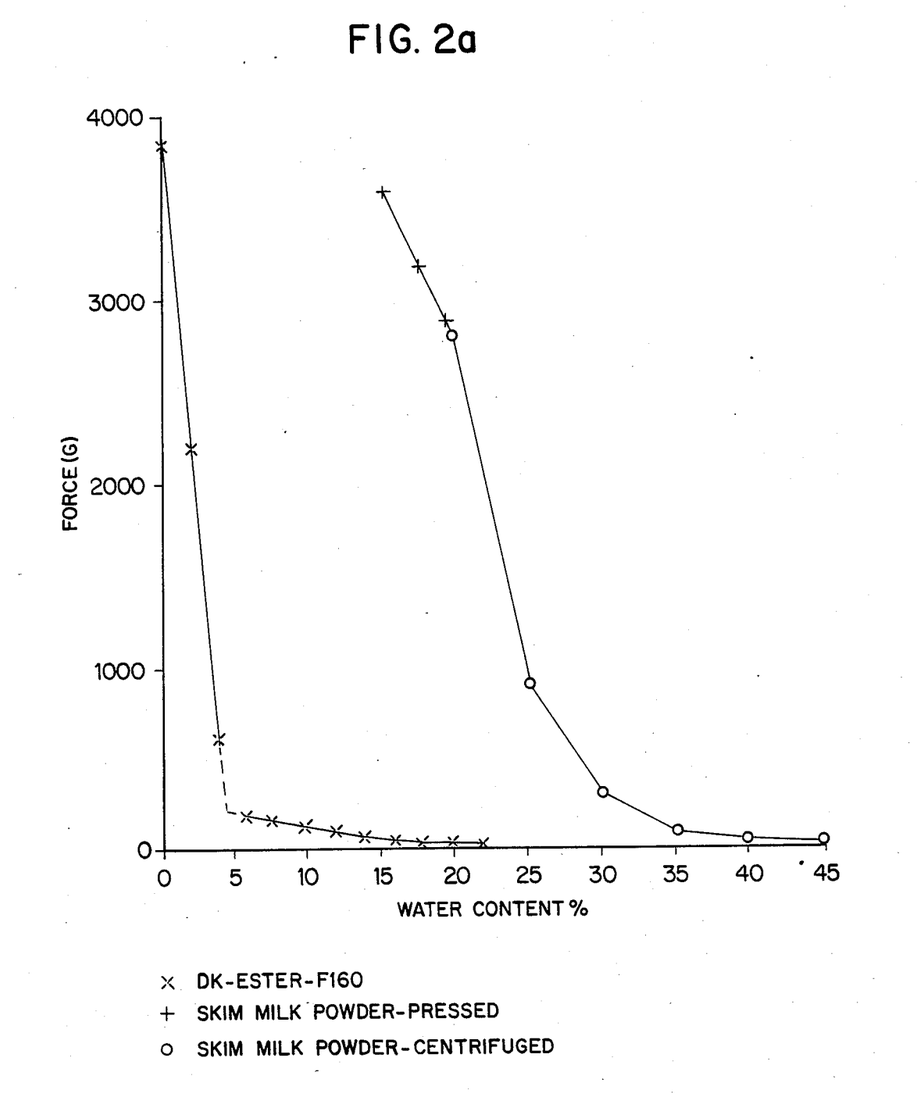
FIG. 2a is a graph showing the variation in critical yield stress of DK Ester F160 with water content.

The results shown in FIG. 2a were obtained by the following method.

Varying quantities of water and DK—Ester-F160 were weighed into vials to make 20 g samples containing from 2-20% water in 2% increments. These mixtures were thoroughly stirred, sealed and heated in a water bath at 60° C. until all the trapped bubbles has been expelled.

The samples were then transferred to a water bath at 39° C. and equilibrated for 1 day. The viscosity was then measured by following the output of a 2 kg strain gauge on a chart recorder, where the strain gauge measures the resistance exerted by the mixture to a $\frac{1}{8}''$ (3.2 mm) diameter hemispherical-ended plunger moving at a velocity of 0.021 mm sec$^{-1}$. The measured force used is when either a maximum is reached or steady state achieved.

The results plotted in FIG. 2a clearly show the marked discontinuity in critical yield stress which occurs at a water content of about 4.5%.

Figure 1:
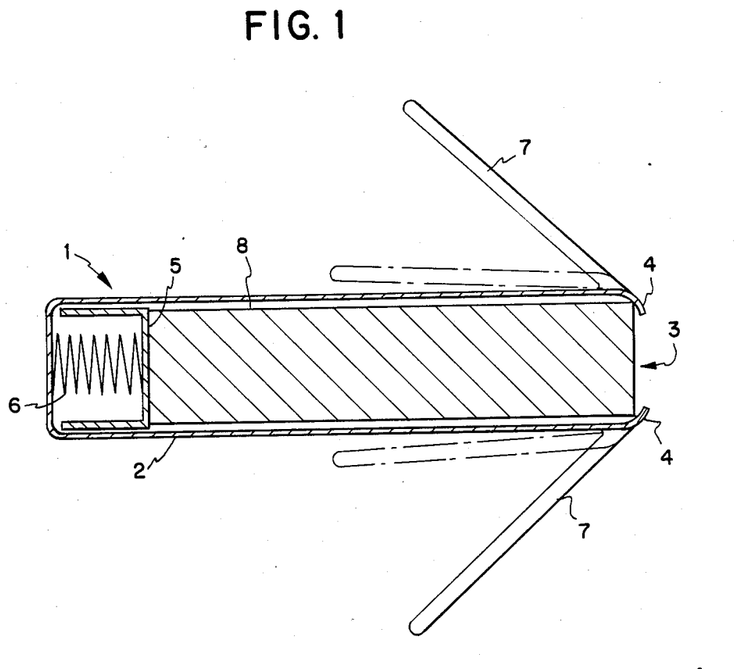
FIG. 1 is a cross sectional view of a controlled release intra-ruminal device (IRD)

FIG. 1 is a cross sectional view of a variable geometry device as disclosed in our aforementioned Pat. No. 520409. The device 1 comprises a tubular body 2 having an opening 3 at one end which opening is restricted by resilient projections 4. Preferably the body has a length of 14 cm. and a diameter of 2.8 cm. for cattle and a length of 9 cm. and protrude inwardly from said one end of the body. The other end of the body is closed. The body contains a cupped plunger 5 which is capable of sliding longitudinally thereof. The plunger is biased by means of a helical spring 6. The helical spring is made from spring steel wire having a circular transverse cross section of 0.5 mm. in diameter. The spring comprises 20 to 30 coils and is capable when fully compressed of exerting a pressure approximately 100 grams per sq.cm. The body has two resilient arms 7 attached thereto at said one end, which arms project outwardly from said body at an angle of approximately 45° to the side thereof to form a first configuration. In the first configuration the device has the shape of an arrowhead. The arms 7 are capable of being resiliently flexed about an axis corresponding approximately with the junction of the arms with the body, to form a second configuration in which the arms are substantially parallel to the length of the body as shown by the dotted lines in FIG. 1. With the arms folded back into the second configuration the device is capable of being administered to cattle per os. As shown in FIG. 1, the body contains a preformed matrix core 8 made in accordance with this invention and containing a therapeutic material. The resilient projections 4 are sufficiently flexible to allow the precast plug to be inserted into the device but have sufficient rigidity to retain the plug within the device against the pressure exerted by the spring. Alternatively, a barrier preventing ejection of the plug by action of the spring can be applied after the plug has been inserted, e.g., a strip of polypropylene welded across the opening 3 of the body. The body 2, arms 7 and projections 4 may be integrally moulded from a suitable plastics material such as polyethylene polypropylene or nylon. By choice of the appropriate material of construction a device may be obtained which can be retained in the rumen indefinitely or for lesser periods of time. For example, a device integrally moulded from low density, low molecular weight polyethylene will eventually fail after about 270 days in the rumen by flex cracking of the arms. On the other hand, a device integrally moulded from polypropylene is virtually indestructable.

Figure 2B:
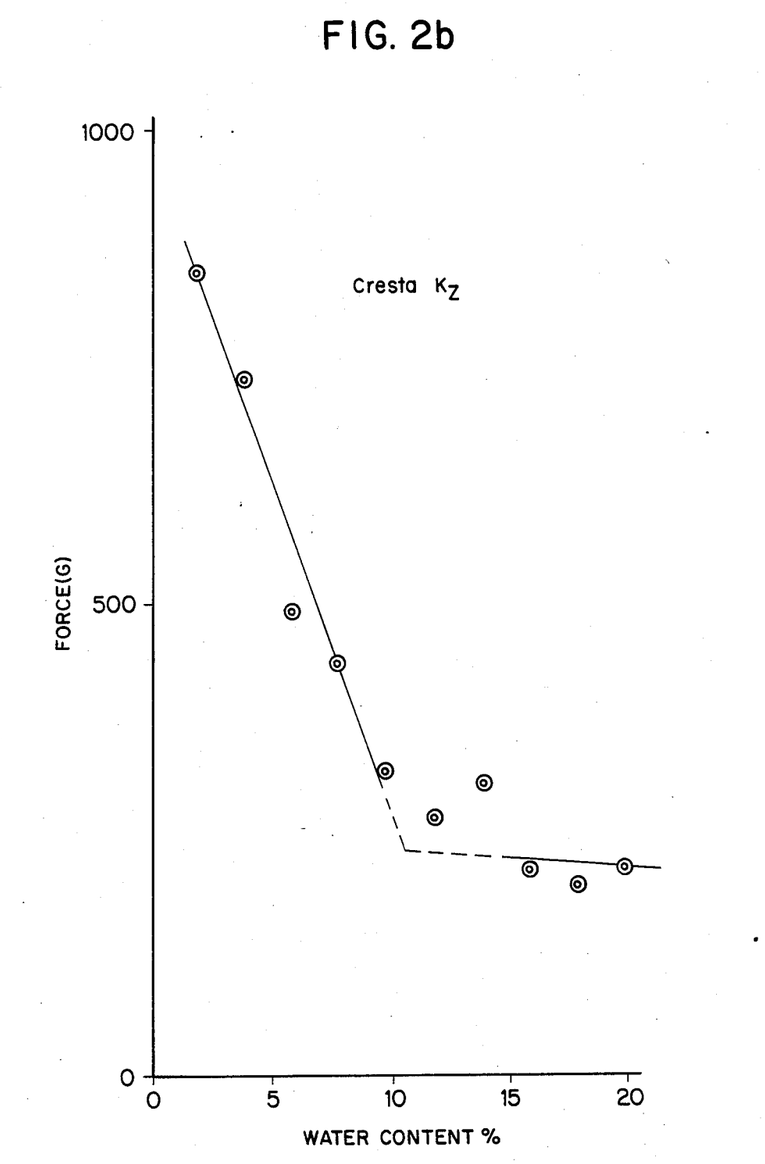
FIG. 2b is a graph showing the variation in critical yield stress of skim milk powder.

By choice of a suitable spring the core can be exposed to an urging force which just exceeds the critical yield stress of the core material at a water content near the discontuinity region (see FIG. 2) thereby causing the material with the lowered critical yield stress to be slowly extruded and subjected to mechanical erosion.

The operation of the device of the present invention will now be described.

The device described above has a cylindrical barrel 2 with a dissolution orifice at one end, against which is held a cylindrical performed matrix 8 core of bioactive material mixed with a dissoluble carrier, using an urging means 6 in the alternative end of the barrel. The dissoluble carrier must be able to form a gel with water which in turn must be able to be extruded through the dissolution orifice by the action of the urging means. The further uptake of water is kinetically limited by the remaining barrier of gel following extrusion and loss of extruded material.

The choice of suitable carrier materials is not limited by the water content of the gels they form. Materials that form gels of greater than about 80% water content (e.g. Carlopols of B.R.Goodrich) may be a core component at the less than about 20% content. The cores should form gels at less than or equal to 40% water content to have the required effect. Thus, the selection of suitable carrier material is determined by the water content of the gels they form. The more water absorbed by the carrier materials so form the gels the less of this material is needed in the therapeutic composition to achieve a desired water content.

Limiting device dimensions and characteristics follow

| Property | Sheep | Cattle |
| --- | --- | --- |
| Length, cm | 6-11 | 10-20 |
| Diameter, cm | 1-2 | 2-4 |
| Orifice diameter, mm | 3-13 | 5-28 |
| Minimum dimension for device retention (width), cm | 3 | 5 |
| If arms are used, total arm lengths, cm | 3-15 | 10-25 |
| Spring length, cm | 10-40 | 10-60 |
| Compressive strength of spring at total compression, G force | 100-600 | 100-1000 |
| Core length, cm | 8 | 17 |
| Core clearance in barrel, mm | 2 | 2 |

In the intraruminal device and composition of the therapeutic agent and carrier in accordance with the present invention, the rate of release of the therapeutic agent is substantially independent of the force of the spring or driving means, and is determined by the choice of carrier material.

Typically, the force of the driving spring is less than 2500 G, preferably between about 100 and 1000 G.

The yield stress of the gelled area or volume or of the gel when formed is less than 2500 G, and typically less than 1000 G or 500 G, preferably about 100 to 1000 G. The rate of release of the therapeutic agent from the device of the present invention is up to about 20 mm per day, typically in the range of 0.1 to 10 mm per day, preferably about 0.5 to 5 mm per day.

The effect of and the relationship between the steep decline in rheological properties with increasing water content and the required gel property of cores for the device will now be described.

The mechanical events that occur on operation of the device in accordance with the present invention.

Water taken up via the dissolution orifice penetrates the core so that the water content of the gel decreases with depth of penetration. At a given water content (4 to 40%, depending on the carrier components used) the core moves forward under the action of the urging means, extruding gel through the orifice at the end of the device at a rate determined by the water content the yield stress of the gel of the orifice equals the net force of the urging means. Extruded gel is lost by dissolution or abrasion. If the change in yield stress is steep with respect to water content, then extrusion stops abruptly, since the force of the urging means is insufficient to overcome the yield stress of the nongelled core, leaving a sharply defined gel layer within the core behind the dissolution orifice. This sharply defined layer of gel is the barrier to further water uptake which occurs at a uniform rate, independent of a reasonably wide range of spring strengths.

The use of complex or multi-holed orifices.

The extrusion processes at the orifice may be considered as extensive deformation of the shoulders of the orifice end of the device which result from the drilling or forming the orifice. The gel must flow across these shoulders at an angle near 90° to the direction of general core movement. Under certain circumstances, this process is limiting, leading to undesirable cavitation of the core at the orifice. This problem is eliminated by, in effect, partly dispersing the orifice within the end of the device, either by having more than one (central) orifice, i.e. 6 further holes round a central circular hole, or non-circular holes with convoluted edges which all act to reduce the dimensions of the shoulder portions across which the gels must deformably extrude. The effect of these complex orifices is kinetically equal to circular orifices of equal area, but in addition, largely eliminate cavitation.

The unexpected results have been observed in our experiments to date using the present cores in IRD's. The first, as reported above, was the unexpected slow rate of dissolution of DK-ester-F160 which has an HLB of 15.

This is a desirable result for long acting IRD's. The other two unexpected results are related to controlled release and are illustrated in the examples which follow.

They are (i) IRD's containing pressed cores have given the most accurately uniform in vivo release rates obtained in our studies (examples 1 and 2) and (ii) between-animal variability, expressed as a standard error of the mean IRD release rate, is an order of magnitude smaller than that usually observed for cast cores in IRD's (example 3).

EXAMPLE 1

In vivo release of compressed matrix from spring driven IRD.

The core was prepared from a spray dried powder CRESTER KZ (Croda), described as a food grade polygylcerol stearate, with a HLB of 6.5–7.5 10 g was weighed into a 1.45 cm diameter dye and pressed with a hydraulic ram to a force of 3000 lb. wt. on the core material, this pressure was sustained for 10 seconds, resulting in a tablet of density 1.08 g/cm³. This core was loaded into a 9.2 cm IRD with 7.9 mm orifice, and then loaded with a spring giving a spring strength of 162 g at 75% compression. The spring chamber was then sealed with a 9.0 mm neoprene stopper to ensure that the chamber was hermetically sealed.

Figure 3:
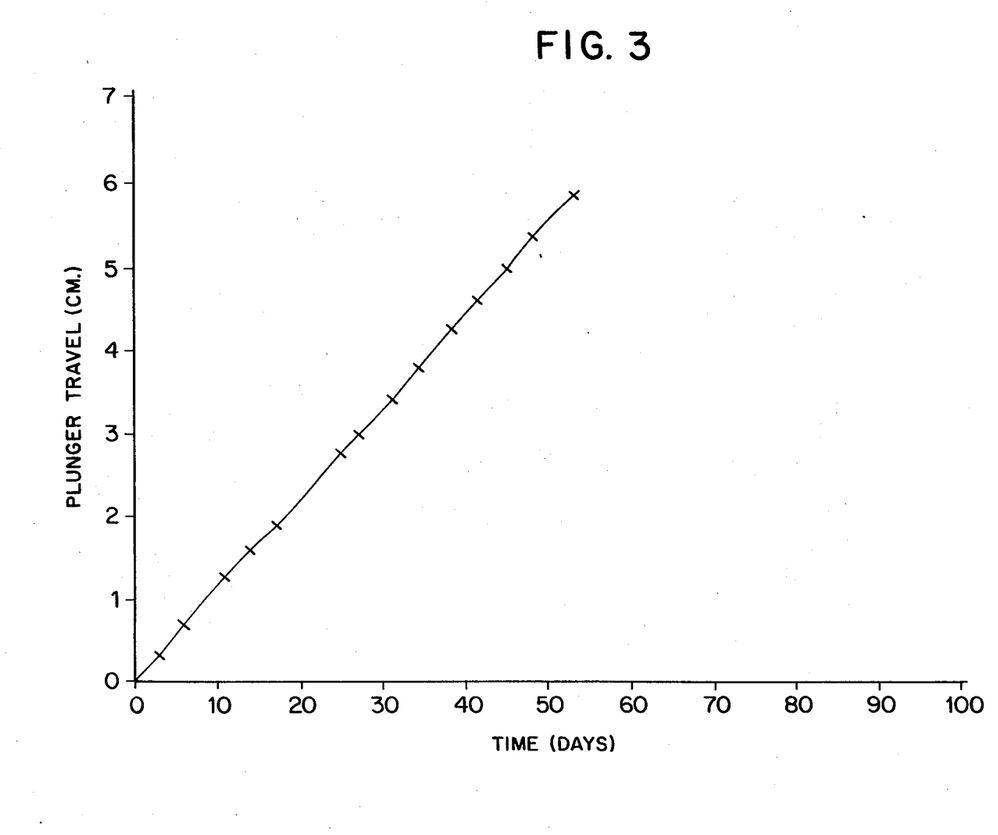
FIGS. 3 and 4 are are graphs showing the in vivo rate of release of material from IRD's containing a core in accordance with the invention.

The IRD was placed in the rumen of a fistulated bovine. The output, i.e., rate of release of material, from the IRD was measured by inspecting the IRD at intervals and measuring the distance travelled by the plunger. FIG. 3 shows the results obtained. The output from the IRD was substantially linear over a period of 60 days.

EXAMPLE 2

Uniformity of release rates in vivo. (Sheep sized IRD's)

Four groups of capsules were prepared as follows.
Group OP containing Oxfendazole (Syntex) 50% w/w in Teric 18M2 (I.C.I.A.L.)
Group O containing Oxfendazole (Syntex) 50% w/w in DK-ester-F160.
Group MP containing Monensin (Eli Lilly) 40% w/w in Teric 18M2.
Group M containing Monensin (Eli Lilly) 40% w/w in DK-ester-F160.

Cores based on Teric 18M2 were prepared as follows. Matrix components were mixed at 60° homogenized using a Silverson homogenizer for 5 minutes, and the mixtures were then evacuated at 60° C. to remove contrained gases. Cores were poured at 60° C. into moulds kept at 15° C. Cores were cut to a length of 5.25 cm and ranged in weight from 9 to 10 g (Oxfendazole) and 9±0.15 g (Monensin). Cores based on F160 were prepared as follows. Matrix components were sieved together through a 35 mesh sieve, mixed on powder mixing paper, weighed into a cylindrical die and pressed at 7000 psi. For Monensin, 1 g tablets were pressed, 9 tablets being inserted per IRD. For Oxfendazole, 5 g and 4 g tablets were pressed, with one of each tablet inserted per IRD. Weight precisions were 9±0.04 g (Monensin IRD's) and 9±0.02 (Oxfendazole IRD's).

Figure 4:
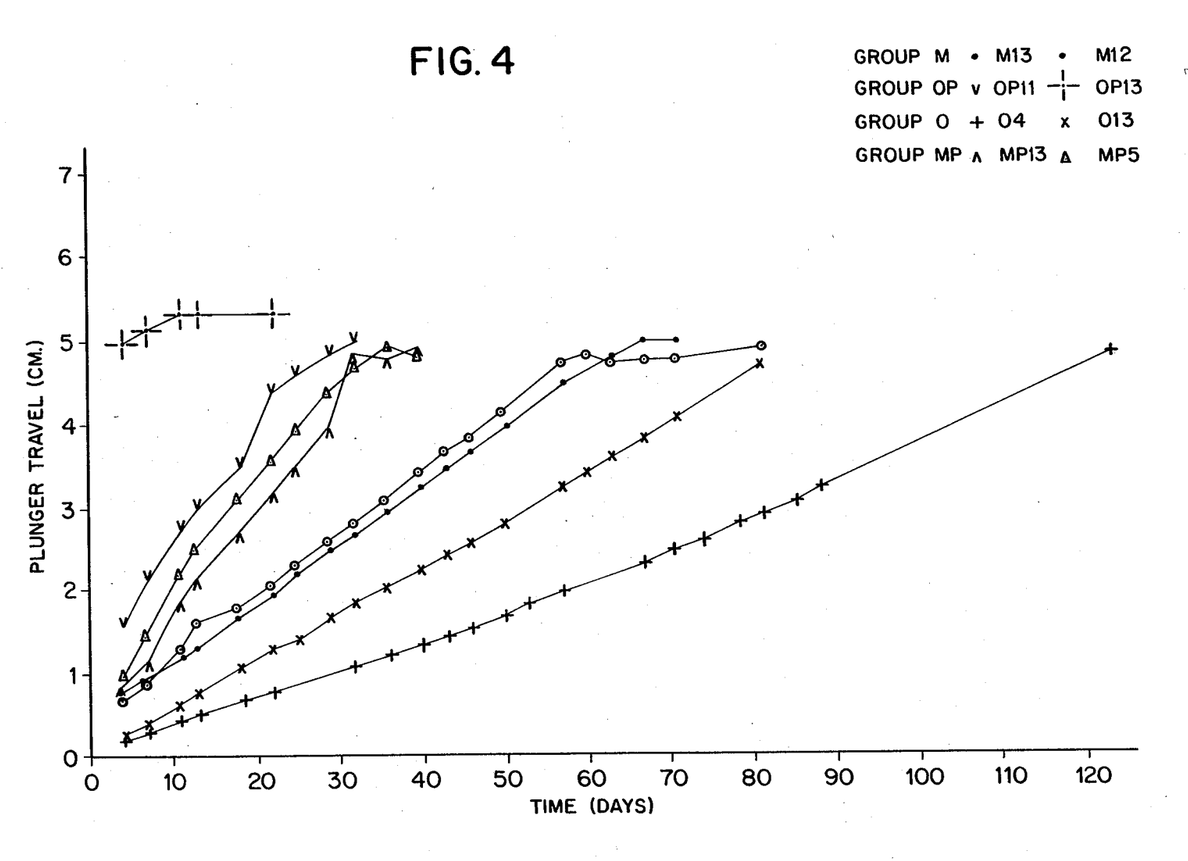

In the IRD's spring strengths at 75% compression were 171 to 181 g. Orifice diameter was 7.9 mm and IRD barrel length was 8 cm. In vivo release of representative duplicate IRD's from the four groups was determined with rumen fistulated cattle, the results shown graphically in FIG. 4, being expressed as plunger travel (cm) with time in vivo.

EXAMPLE 3

Between-animal variability studies with sheep.

The remainder of the capsules prepared as described in Example 2 were does to 12 sheep (one capsule per group to each animal). Capsules were recovered at slaughter on day 45 and analysed to provide the following data of measured loss of total matrix (g).

| Capsule group | O | OP | M | MP |
|---|---|---|---|---|
| X̄ (Mean matrix loss) g | 2.57 | 2.45 | 5.32 | some capsules empty |
| SEM (standard error of mean) | 0.065 | 0.772 | 0.066 | |
| $\frac{SEM}{\overline{X}}$ | 0.026 | 0.32 | 0.013 | |

Experiments of this design using cast cores in sheep IRD's gave results comparable with the OP group with one exception, when cast cores containing Oxfendazole (8% w/w) in the surfactant mixture Span 60/Tween 80 (60:40) (I.C.I. Australia Ltd.) gave the ratio SEM/X̄=0.0231 (6 sheep).

EXAMPLE 4

The variation in yield stress with water content of the carrier materials DK-ester-F160, Cresta KZ and skim milk powder (commercial sample).

The Measurement of Yield Stress

The yield stress of water-gelled carrier materials was measured using a penetrometer in which the penetration probe was a thin rod (2 mm diameter) with a sphere of diameter 3.2 mm on the end which penetrated the gelled sample. The rod was mounted on the sensor of a 2 kg non-bonded strain gauge and the gauge plus sensor assembly driven downward (probe foremost) at a constant speed of 0.0213 mm sec$^{-1}$ through the gelled sample. The yield stress was the resistance to the movement of the sphere through the gel (or flow of gel past the sphere) at the travel rate of 0.0213 mm sec$^{-1}$. The system is therefore analogous to a falling sphere viscometer except that the viscosity is far too high for the sphere to fall through the gelled sample under its own weight at a measurable rate. The uncorrected viscosity would, by this analogy, be given by $$\eta = Fg/6\pi rv$$

(the falling sphere equation)
where
  $\eta$ = the fluid viscosity
  F = the force on the sphere (the buoyancy-corrected weight of the sphere in the falling sphere acceleration)
  g = the gravitational acceleration
  r = sphere radius
  v = velocity of sphere movement through gel.

To avoid complex corrections, the data presented herein is the force on the sphere rather than viscosity.

The Preparation of Gels
(a) Dk-ester-F160 and Cresta KZ

Varying quantities of water and carrier were weighed into vials to make 20 g samples containing from 0 to 20% water. The mixtures were thoroughly stirred, sealed and heated in a water-bath at 60° C. until trapped bubbles were expelled.

The samples were then incubated using a Waring blender to produce either force flowing powders (water contents less than 19%) or pastes (water contents 20 to 45%). The powder mixtures were pressed as described in Example 1 to produce cylindrical cores and the pastes were centrifuged at 29,000 g for 1 minute to produce coherent plugs. Resultant cores and plugs were incubated at 39° C. for 4 to 24 h prior to viscosity measurement.

RESULTS

FIGS. 2a and 2b show the variation in yield stress (g force) against water content (%) for the three carrier materials.

DISCUSSION

The variation in yield stress with water content of the gelled core of a IRD of this invention is a most important property, determining reproducibility and linearity of the devices.

As water diffuses into the core of an IRD when first inserted into the rumen, yield stress will fall at the orifice until it equals the net spring force at the orifice. Extrusion is thus initiated, and continues at steady state, extruded matrix being removed as the capsule moves through the rumen contents.

When a carrier material is characterized by a very steep fall in yield stress with increasing water content (FIGS. 2a and 2b) the water content at the point of extrusion is relatively independent of the net spring force at the orifice causing the extrusion. Similarily, since the role of diffusion of water to achieve that critical water content at which extrusion occurs is dependent only on the temperature and the concentration gradient of water in the core of the IRD (which will be dependent only on that critical water content) then the diffusion rate itself is relatively independent of net spring force at the orifice.

Thus release rate of the IRD will be constant (linear output) independent of spring strength over the operational life of the device. Likewise, IRD reproducibility, much of which is a reflection of factors affecting net spring force at the orifice, is greatest for steepest decline in yield stress with water content.

The following examples illustrate that the gelling of the solid therapeutic agent and carrier are in the region of the orifice and not the urging force of the spring determines the rate of administration of the therapeutic agent.

These examples illustrate that spring strength, within a reasonably wide range has no observable effect on release rate.

EXAMPLE 5

5 springs of length 10–32 cm were prepared as defined in Table 1:

TABLE 1

| Spring Length cm | Compressive Strength G. Force | |
|---|---|---|
| | at beginning (100% compression) | at end (6 cm extension) |
| 10.0 | 140 | 49 |
| 15.0 | 169 | 110 |
| 20.1 | 189 | 145 |
| 25.1 | 195 | 160 |
| 32.0 | 207 | 179 |

These springs are the urging means in sheep-sized IRD's with a 9.5 mm orifice diameter and cores of $Cr_2O_3$ (50% w/w) in Dai-Ichi Kogyo Seiyaku DK-ester-F160.

In vivo release rates were 1.44±0.04 mm d$^{-1}$ (for days 0–10) at 1.13±0.04 mm d$^{-1}$ (for days 20–30).

EXAMPLE 6

8 springs of length 24–38 cm were tested as in Example 5. Spring characteristics are given in Table 2.

TABLE 2

| Spring length, cm | Spring strength, 100% Compression, G force |
|---|---|
| 23.5 | 139 |
| 29.5 | 139 |
| 30.3 | 172 |
| 35.0 | 190 |
| 38.0 | 195 |
| 29.7 | 210 |
| 29.5 | 230 |
| 29.0 | 330 |

In vivo release rates for day 0–22 were 1.30±0.04 mm d$^{-1}$. Thus, from the foregoing it can be seen that there is a constant release rate for the device irrespective of the urging force of the spring used in the device. It is the property of the carrier which determines the release rate and hence the rate at which the therapeutic agent is administered.

We claim:

1. A controlled release composition for administering a therapeutic agent to a ruminant comprising the therapeutic agent and a carrier material in the form of a coherent tablet or bolus in solid form, wherein said carrier material is formed from a non-tacky free flowing powder which forms a gel in contact with an aqueous medium in which 90% of the particles are less than 100 µm (200 mesh sieve) and which can be mixed with the therapeutic agent to give a uniform, intimate and reproducible mixture such that when the tablet or bolus contacts an aqueous medium a fluid from the aqueous medium is absorbed at the tablet/aqueous medium interface into the body of the tablet to a predetermined depth of penetration so as to produce a gelled volume contiguous with the interface corresponding to the depth of penetration of the fluid, said gel hindering further penetration of the fluid into the tablet beyond the prearranged depth in order to maintain the rate of fluid penetration constant and the integrity of the tablet beyond the prearranged depth of penetration of the fluid to prevent release of therapeutic agent therefrom and said gel having a yield stress which is substantially less than the yield stress of the corresponding volume of the tablet before gelling and which sharply declines with increasing water content up to a preselected critical water content thereby permitting controlled release of therapeutic agent from the gel in use.

2. A controlled release composition according to claim 1 further comprising a bonding and/or slip agent.

3. A controlled release composition according to claim 1 in which the tablet or bolus is formed in a die under pressure.

4. A controlled release composition according to claim 1 in which the yield stress of the gel declines gradually as the water content is increased above the critical water content.

5. A controlled water release composition according to claim 1 in which the fluid is an aqueous solution from the rumen of the ruminant.

6. A controlled release composition according to claim 1 in which the carrier material has a softening point greater than 39° C. when in the rumen of a ruminant.

7. A controlled release composition according to claim 1 in which the critical water content is greater than 4%.

8. A controlled release composition according to claim 1 in which the critical water content is in the range from greater than 4% to about 40%.

9. A controlled release composition according to claim 1 in which the carrier material is a surface active material or an emulsifying agent.

10. A controlled release composition according to claim 1 in which the carrier material is selected from the group comprising a sucrose ester, polyglyceryl stearate, and milk powder.

11. A controlled release composition according to claim 10 in which the sucrose ester is a monosteorate ester.

12. A controlled release composition according to claim 1 in which the yield stress of the gelled area of the tablet or bolus is less than 2500 G.

13. An intraruminal device for administering a therapeutic agent to a ruminant comprising a hollow body having an opening located at one end, a solid tablet or bolus comprising the therapeutic agent and a carrier material contained within the body, a driving means for urging the tablet or bolus towards the opening, restricting means adjacent the opening for preventing expulsion of ungelled tablet or bolus from the device by said drving means, and retaining means connected to the body for retaining the device in the rumen of the ruminant after location therein, said carrier material being in the form of a coherent tablet or bolus in solid form, wherein said carrier material is formed from a non-tacky free flowing powder which forms a gel in contact with an aqueous medium in which 90% of the particles are less than 100 µm (200 mesh sieve) and which can be mixed with the therapeutic agent to give a uniform, intimate and reproducible mixture such that when the tablet or bolus contacts an aqueous medium a fluid from the aqueous medium is absorbed at the tablet/aqueous medium interface into the body of the tablet to a predetermined depth of penetration so as to produce a gelled volume contiguous with the interface corresponding to the depth of penetration of the fluid, said gel hindering further penetration of the fluid into the tablet beyond the prearranged depth in order to maintain the rate of fluid penetration constant and the integrity of the tablet beyond the prearranged depth of penetration of the fluid to prevent release of therapeutic agent therefrom and said gel having a yield stress which is substantially less than the yield stress of the corresponding volume of the tablet before gelling and which sharply declines with increasing water content up to a preselected critical water content thereby permitting controlled release of therapeutic agent from the gel in use.

14. An intraruminal device as claimed in claim 13 wherein the force exerted on the tablet or bolus by the driving means is sufficient to extrude the therapeutic agent from the gel through the opening of the body.

15. An intraruminal device as claimed in claim 13 wherein the force exerted by the driving means is insufficient to extrude an ungelled composition through the opening of the device.

16. An intraruminal device as claimed in claim 13 in which the rate of release of the therapeutic agent is up to about 20 mm per day.

17. An intraruminal device as claimed in claim 13 in which the rate of release is in the range of 0.1 to 10 mm per day.

18. An intraruminal device as claimed in claim 13 in which force of the driving means is less than 2500 G.

19. An intraruminal device as claimed in claim 13 in which the force of the driving means is in the range of 100 to 1000 G.

20. An intraruminal device as claimed in claim 13 in which the release rate of the therapeutic agent is substantially independent of the force of the driving means.

21. An intraruminal device according to claim 13 in which the retaining means in a resilient member connected to the body of the device so as to be capable of two different configurations, a first configuration in which the resilient member is relatively close to the body so that the device is capable of being administered to the ruminant and a second configuration in which the resilient member extends from the body so as to be retained the rumen after location therein.

22. In combination a therapeutic composition comprising a therapeutic agent and carrier material in the form of a coherent tablet or bolus in solid form, wherein said carrier material is formed from a non-tacky free flowing powder which forms a gel in contact with an aqueous medium in which 90% of the particles are less than 100 μm (200 mesh seive) and which can be mixed with the therapeutic agent to give a uniform, intimate and reproducible mixture such that when the tablet or bolus contacts an aqueous medium a fluid from the aqueous medium is absorbed at the tablet/aqueous medium interface into the body of the tablet to a predetermined depth of penetration so as to produce a gelled volume contiguous with the interface corresponding to the depth of penetration of the fluid, said gel hindering further penetration of the fluid into the tablet beyond the prearranged depth in order to maintain the rate of fluid penetration constant and the integrity of the tablet beyond the prearranged depth of penetration of the fluid to prevent release of therapeutic agent therefrom and said gel having a yield stress which is substantially less than the yield stress of the corresponding volume of the tablet before gelling and which sharply declines with increasing water content up to a preselected critical water content thereby permitting controlled release of therapeutic agent from the gel in use and a device for administering the therapeutic agent.

* * * * *